United States Patent
Roche et al.

(10) Patent No.: US 8,323,226 B1
(45) Date of Patent: Dec. 4, 2012

(54) MULTILAYER LIMB SLEEVE LINER

(76) Inventors: Martin William Roche, Fort Lauderdale, FL (US); Alvin S. Blum, Fort Lauderdale, FL (US)

( * ) Notice: Subject to any disclaimer, the term of this patent is extended or adjusted under 35 U.S.C. 154(b) by 119 days.

(21) Appl. No.: 12/799,161

(22) Filed: Apr. 20, 2010

Related U.S. Application Data

(63) Continuation-in-part of application No. 11/324,485, filed on Jan. 3, 2006, now abandoned, and a continuation-in-part of application No. 11/228,880, filed on Sep. 16, 2005, now abandoned.

(51) Int. Cl.
*A41B 11/02* (2006.01)
*A43B 17/00* (2006.01)

(52) U.S. Cl. ............. 602/62; 602/60; 602/63; 2/239; 2/242

(58) Field of Classification Search .......... 602/5, 12, 602/23, 27–29, 60–63, 65, 75–77; 128/882; 2/22, 59, 272, 911, 61, 239–242; 36/1.5, 36/2 R; 66/169 R–171, 177, 178 A, 178 R, 66/183–188, 192, 193, 195, 202; 442/1, 442/2, 181–186

See application file for complete search history.

(56) References Cited

U.S. PATENT DOCUMENTS

| | | | | |
|---|---|---|---|---|
| 2,238,804 | A | * | 4/1941 | Brown .................. 36/10 |
| 4,771,768 | A | | 9/1988 | Crispin |
| 5,242,379 | A | | 9/1993 | Harris |
| 5,370,133 | A | | 12/1994 | Darby |
| 6,311,334 | B1 | | 11/2001 | Reinhardt |

* cited by examiner

*Primary Examiner* — Kevin C Sirmons
*Assistant Examiner* — Keri J Nelson
(74) *Attorney, Agent, or Firm* — Alvin S. Blum

(57) ABSTRACT

The invention provides a multilayer sleeve liner for application to the skin of a limb before applying a cast or brace. The liner is readily conformable to the limb configuration. It has a first layer that is applied to the skin. This has protective and cushioning functions. A second layer has a mesh structure that encircles the limb. It is constructed so that when its first end is pulled away from its second end, the encirclement of the limb is tightened. When one end of the mesh is attached to one end of the cast, and the other end is attached to another end of the cast, tension on the limb will tighten the liner. Without removing the cast, the liner may be adjusted by releasing one end of the mesh from the cast, and increasing or decreasing tension as necessary, then reattaching the mesh to the cast. A third layer may be provided to prevent adhesion of the cast to the liner.

6 Claims, 5 Drawing Sheets

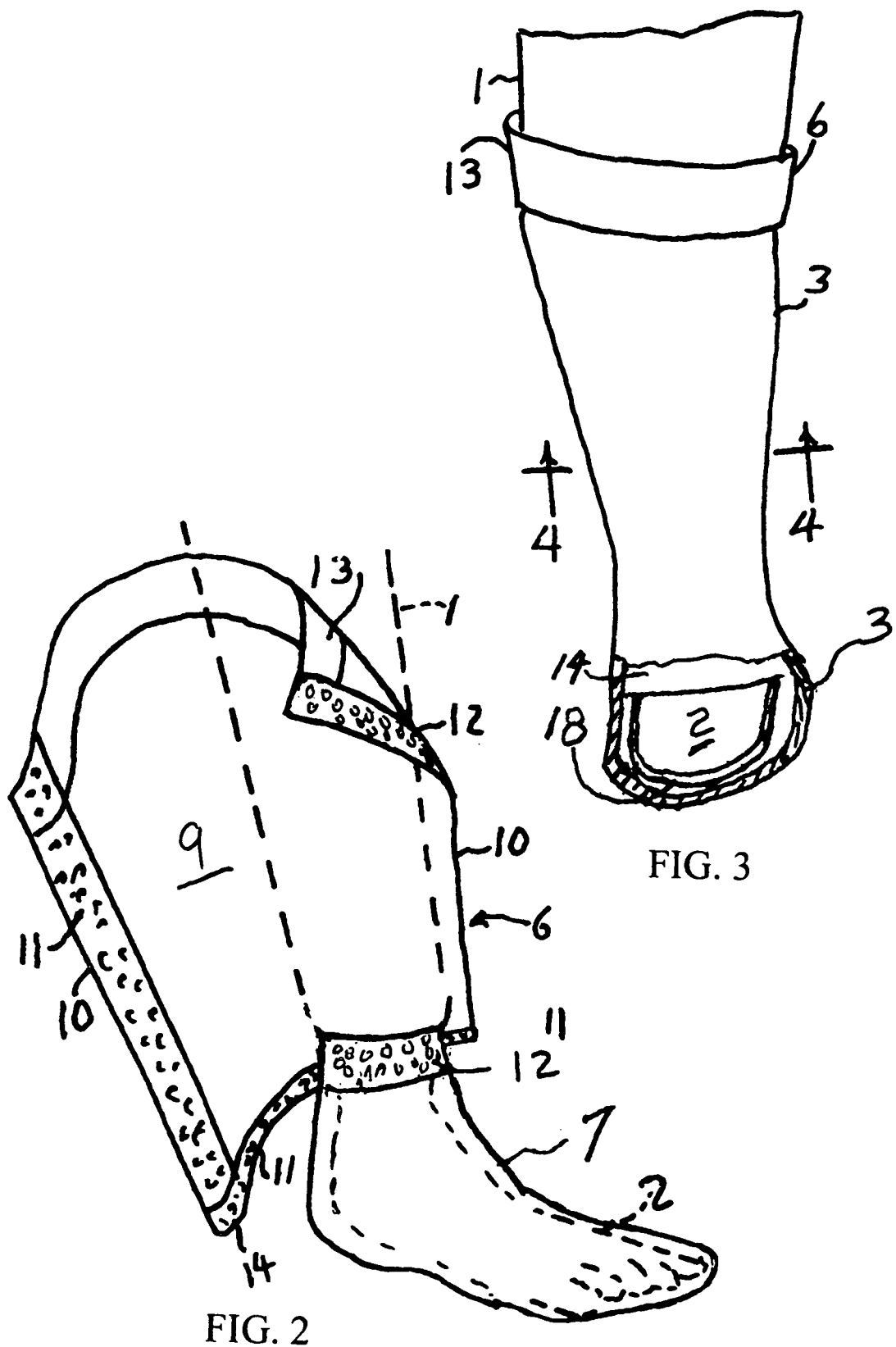

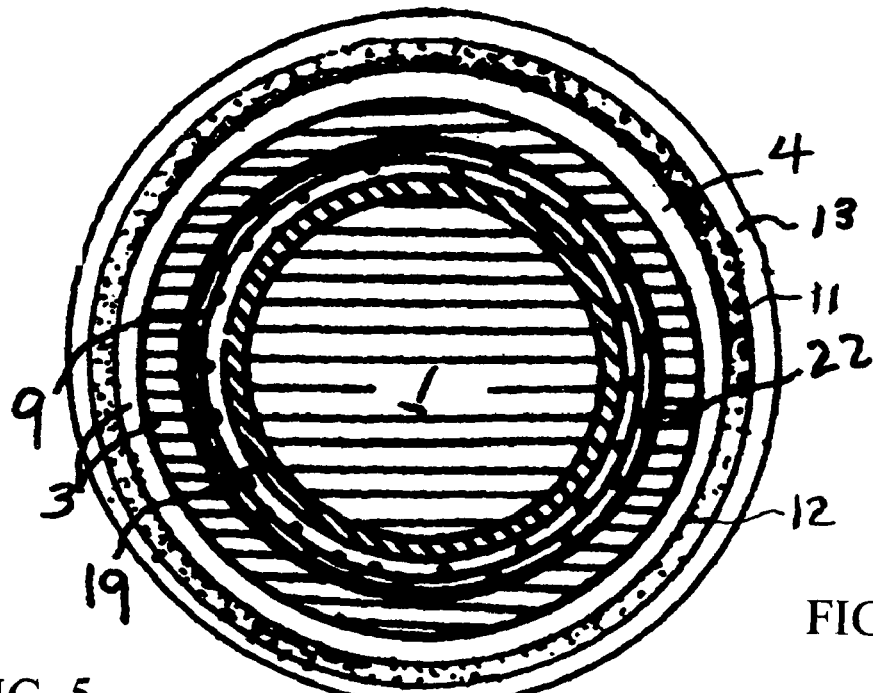
FIG. 4
FIG. 5
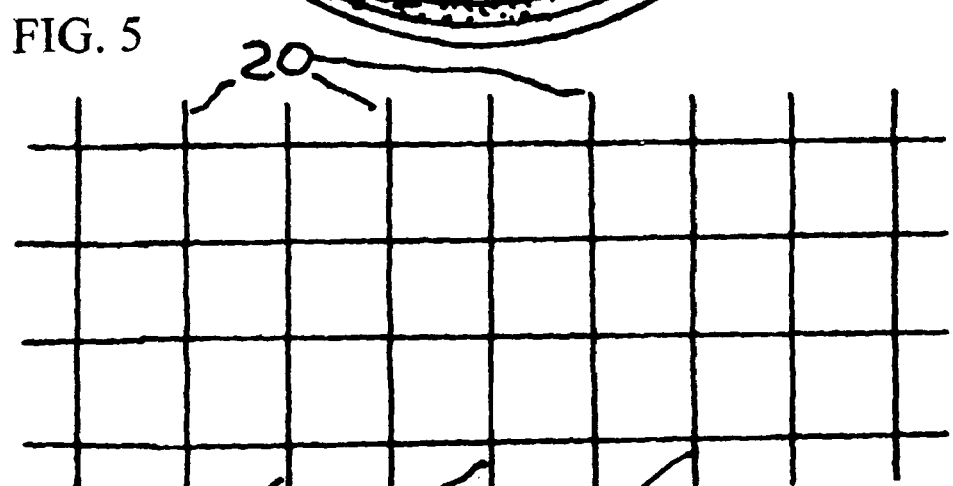
FIG. 6
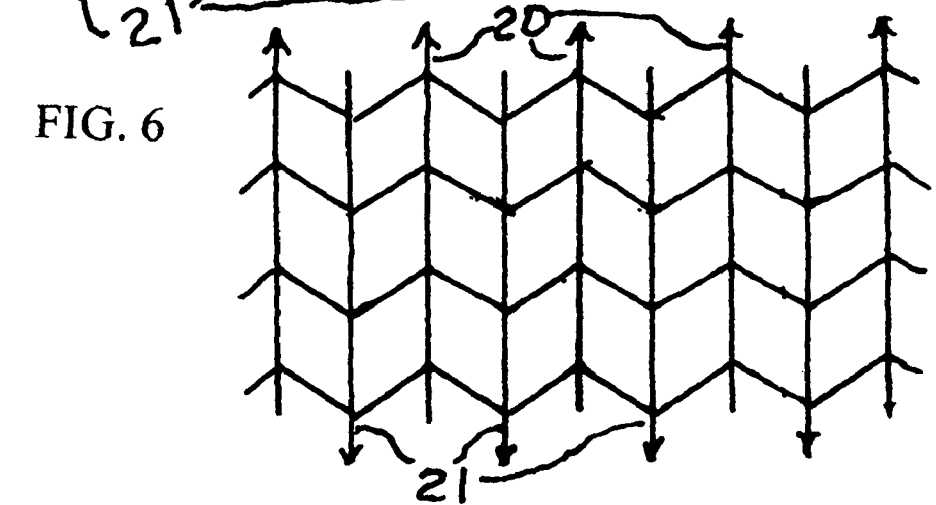

MULTILAYER LIMB SLEEVE LINER

This application is a continuation in part of utility patent application Ser. No. 11/324,485 filed Jan. 3, 2006 now abandoned, that is a continuation in part of utility patent application Ser. No. 11/228,880, filed Sep. 16, 2005 now abandoned, incorporated herein by reference.

BACKGROUND OF THE INVENTION

This invention relates to braces and casts on limbs, and more particularly to liners interposed between the limb and the brace or cast. When a cast or brace is applied to a limb, a liner is generally first applied to the limb to protect the skin. The term cast will be used hereinafter to designate both cast and brace for convenience. The cast is then applied over the liner with sufficient tightness so that it will not be displaced. The cast may be adherent to the liner. Care must be exercised to avoid applying the cast so tight that it impairs circulation. In many situations the cast is applied when the limb is swollen. When the swelling subsides, the cast may be so loose that it moves about, possibly injuring the underlying skin, and loses it efficacy. It may be necessary to replace the cast to correct the problem.

Adjustable elastic stockings were disclosed in U.S. Pat. No. 3,605,122 issued Sep. 20, 1971 to Meyers. They facilitate application of the stocking and provide adjustment to conform to various leg shapes, sizes, and dressings that may be on the leg. A conventional foot portion of the stocking is attached to a unique elastic leg engaging portion. The leg engaging portion is an elastic member having two longitudinal edges that overlap when the member is wrapped around the leg. The edges are provided with hook and loop fasteners to hold the member around the leg with whatever pressure is desired. It would be useful if some sort of mechanism could be provided for a cast liner to adjust its fit without removing the cast.

SUMMARY OF THE INVENTION

Casts and braces are applied to limbs with some sort of inner liner to protect the skin and muscle from injury. The limb may swell or shrink inside the rigid cast. If the cast is loose, the limb will move inside the device. If the cast is too tight it will impair circulation. These effects may cause discomfort and injury. It is an object of the invention to provide a multilayer inner liner that will overcome some of these problems by providing a unique liner that is readily conformable to the limb configuration. It is another object that the liner be able to adjust its fit on the limb without removing the cast.

A limb engaging portion of the liner includes a mesh fabric member encircling the limb. The mesh fabric member has two ends. It is so constructed that when tension is applied between the two ends, the encirclement of the limb is tightened. This mechanism may be employed to tighten or loosen the liner at any time without removing the cast, and also in the initial application of the cast. To maintain the tension, there is provided attaching means for removably attaching one or both ends to the cast. The mesh fabric member may have a plurality of parallel first fibers extending from an upper end element to a lower end element and a plurality of parallel second fibers disposed transverse to the first fibers and extending from the upper end element to the lower end element to thereby form a mesh configuration. The mesh fabric may be woven with the intersections of the first fibers with the second fibers fixed or free to move against each other. The mesh fabric may be a non-woven material with the intersections fixed. The angle between the first and second fibers may be ninety degrees or another angle. The mesh fabric may be provided in a cylindrical form. Alternatively, the mesh fabric may be provided flat with two longitudinal edges that overlap when the mesh fabric is wrapped around the leg. The edges are provided with hook and loop fasteners or other fastening means to hold the member around the limb with whatever pressure is desired.

A layer of material adjacent the outer surface of the mesh fabric member may be provided that prevents adhesion of the body of the mesh fabric member to the cast.

The liner is provided with a skin contacting layer beneath the mesh fabric member to protect the skin and cushion the movement and compression forces of the mesh fabric member. The skin contacting layer may be a resilient membrane that has properties most suitable to skin contact such as vapor transmission and reduced slippage. This may include features such as those disclosed in U.S. Pat. No. 3,983,870 issued Oct. 5, 1976 to Herbert et al.

In an alternative embodiment of the invention, the liner may include a mesh fabric member having two longitudinal edges that overlap when the member is wrapped around the limb, and two terminal elements at the ends transverse to the edges. The edges are provided with hook and loop fasteners to hold the member around the limb with whatever pressure is desired. The member has a plurality of parallel longitudinal fibers attached to a plurality of transverse fibers at their intersections. Alternate longitudinal fibers are unattached to a second terminal element and are attached to a first terminal element and the other longitudinal fibers are attached to the second terminal element, and unattached to the first terminal element. When the two elements are being forced away from one another, the alternate fibers will be pulled in opposite directions. This will cause the transverse fibers to be moved from their straight path to a convoluted path that is shorter in overall length. The short overall length of the transverse fibers results in a decrease in the width of the member. Since the member is wrapped around the limb, the net result is a tightening of the member around the limb. When the liner is used with a brace that encloses a joint, the mesh fabric member may have the active longitudinal fibers that tighten limited to the sides of the joint so that flexing of the joint does not tighten the liner.

These and other objects, features, and advantages of the invention will become more apparent when the detailed description is studied in conjunction with the drawings, in which like elements are designated by like reference characters in the various drawing figures.

BRIEF DESCRIPTION OF THE DRAWINGS

FIG. 2 is a perspective view of the liner of the invention on a leg shown in phantom.

FIG. 3 is a perspective view of the leg of FIG. 2 with a cast over the liner.

FIG. 4 is a sectional view through line 4-4 of FIG. 3.

FIG. 5 is a detail diagram of the mesh fabric member before compression.

FIG. 6 is a detail diagram of the mesh fabric member during compression.

DETAILED DESCRIPTION OF PREFERRED EMBODIMENTS

Figure 1:
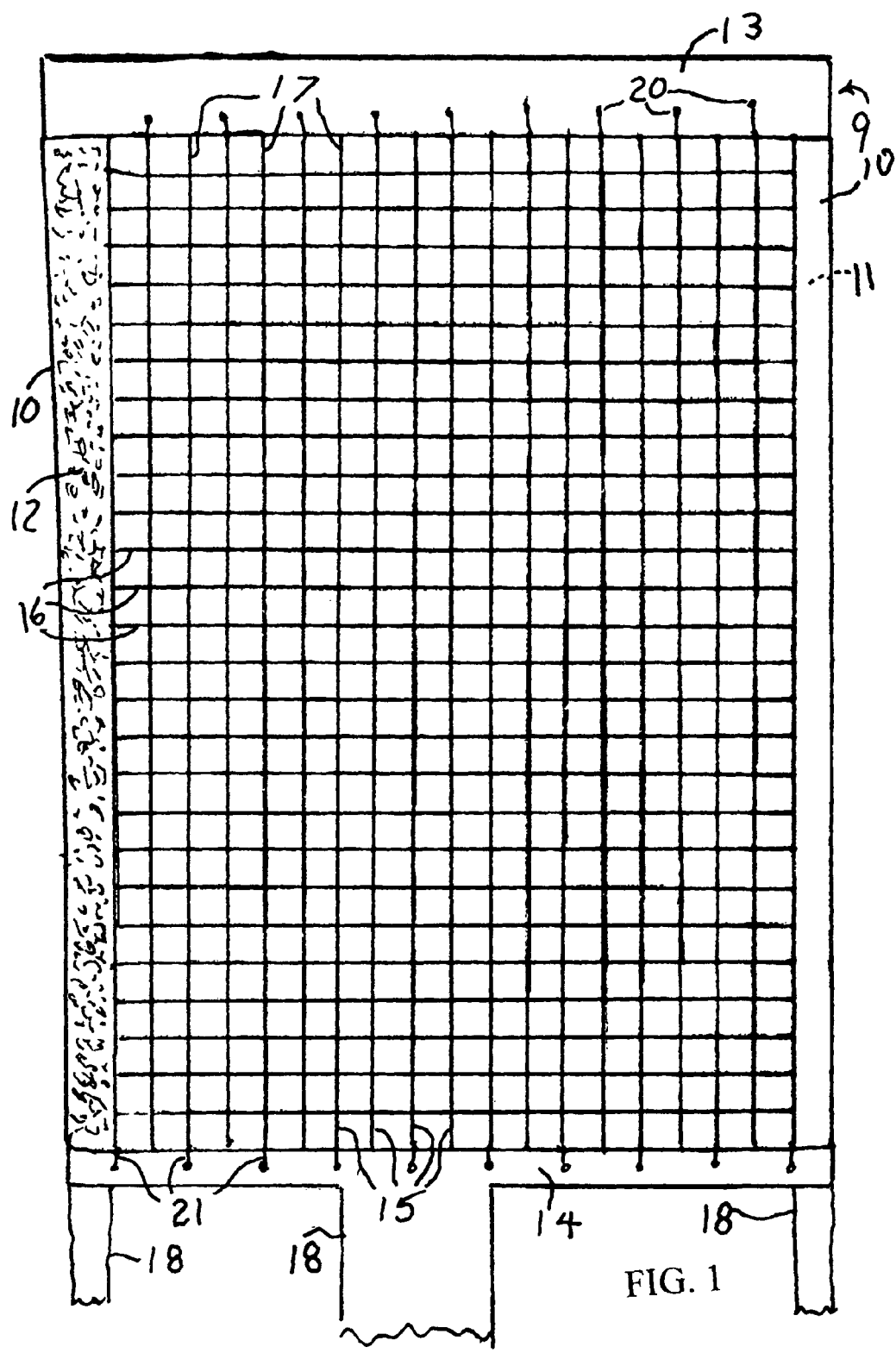
FIG. 1 is a plan view of the limb engaging mesh fabric member of the invention.

Referring now to the drawing FIGS. 1-6, a rigid cast 3 encircles the foot 2 and leg 1 of a person. A soft, resilient, liner 6 is interposed between the skin surface and the rigid cast to protect the limb skin, and to absorb perspiration. The liner 6 of the invention is comprised of a soft, resilient layer inner layer 19, and an outer, wrap around limb-engaging member 9. The inner layer may be fitted and applied to the skin first. The outer limb-engaging member 9 has two longitudinal edges 10 that overlap when the member is wrapped around the leg 1. The edges 10 are provided with hook portion 11 and loop portion 12 of a longitudinal fastener. They cooperate to wrap and secure the member snugly around the limb, while accommodating any size and shape of leg and any dressing that may be in place. The member 9 has a plurality of parallel longitudinal fibers 15 and a plurality of parallel transverse fibers 16 attached to the fibers 15 at their intersections 17. The transverse fibers 16 are attached at their ends to the edges 10. Terminal element 13 at the top of the member 9 and terminal element 14 at the bottom of the member 9 are attached to the longitudinal fibers by means well known in the art such as stitching, cementing, or the like to provide the variably compressive function. As shown, the longitudinal fibers are unattached, or free, at one end with the other end affixed alternately to the upper termination and the lower termination. Alternate fibers 20 are attached to the top element 13. The fibers 21 between those fibers 20 are attached to the lower element 14. The lower element 14 may be attached to a sock portion 7 of the liner as shown in FIG. 2. Alternatively, as shown in FIGS. 1 and 3, the lower portion 14 may be provided with straps 18 that pass under the foot, or attach to a lower end of the cast, boot or shoe. The upper termination 13 is larger in diameter than the limb engaging member 9, and is provided with releasable attaching means (hooks 11) so as to be folded over the top of the cast, and then attached, to the loops 12 on the outer surface of the top 4 of the cast as shown (with a portion of 13 cut away in FIG. 3), and then to later be released, the longitudinal tension readjusted, and then folded over and reattached as required by the swelling of the limb, without removing the cast.

The member 9 has a plurality of parallel longitudinal fibers 15 and a plurality of parallel transverse fibers 16 attached to the fibers 15 at their intersections 17. The transverse fibers 16 are attached at their ends to the edges 10. Terminal element 13 at the top of the member 9 and terminal element 14 at the bottom of the member 9 are attached to the longitudinal fibers to provide the variably compressive function. Alternate fibers 20 are attached only to the top element 13. The fibers 21 between those fibers 20 are only attached to the lower element 14. The lower element 14 may be attached by to a sock portion 7 of the liner as shown in FIG. 2. Alternatively, the lower portion 14 may be provided with attaching means in the form of straps 18 that pass under the foot, or attaching means that attach to a boot or shoe. The upper element 13 is folded over and then attached to the outer surface of the top 4 of the cast as shown in FIG. 3 by attaching means such as for example, the hook 11 and loop fasteners 12 shown.

When the body weight is applied to the foot, the lower element 14 is pulled down relative to the top element 13 attached to the top of the cast or brace. The transverse fibers 16, usually snuggly encircle the limb in a straight line as shown in FIG. 5. When the foot and fibers 21 are forced down relative to the top of the cast and the fibers 20, the transverse fibers 16 are forced into from their straight path into the non-straight path shown in FIG. 6. This draws the vertical fibers closer together as the overall length of the transverse dimension is reduced. This mechanism compresses the encircling member at every step, gripping the leg, and preventing the leg from sliding down in the cast. The transverse fibers are forced back into a straight line by the elasticity of the leg when the weight is removed from the foot, thereby reducing the compression. This periodic compression with every step provides the necessary support of the cast by the soft tissue while reducing forces of the body weight on the bones. Consequently, the mesh does not need to be so tight to hold the leg securely at rest.

The mesh fabric member 9 may be woven or extruded in a planar mesh. It may be formed at first with all of the longitudinal fibers 20 and 21 attached to both the lower terminal element 14 and the top terminal element 13. After forming, alternate longitudinal elements may then be cut at their connections to the alternate terminal elements at that portion of the mesh fabric member 9 where the compression action is desired. This may be useful when the liner is applied to a brace at a joint. When the liner is used with a brace that encloses a joint, the mesh fabric member may have the active longitudinal fibers that tighten limited to the sides of the joint so that flexing of the joint does not tighten the liner.

Referring now to FIG. 4, an inner skin contacting layer1 9 interposed between the skin and the inner surface of mesh fabric member 9 is provided for the liner. The layer 19 may provide cushioning to distribute the compressive forces of the compressive fibers of member 9 over a greater area of skin to lessen their affect on the skin. Layer 19 is adjacent to, but not fixed to, member 9 so that it does not move as much against the skin. This provides further protection for the limb. An outer layer 22 applied to the outer surface of the layer 9 protects the layer 9 from adhesion to the cast.

Figure 7:
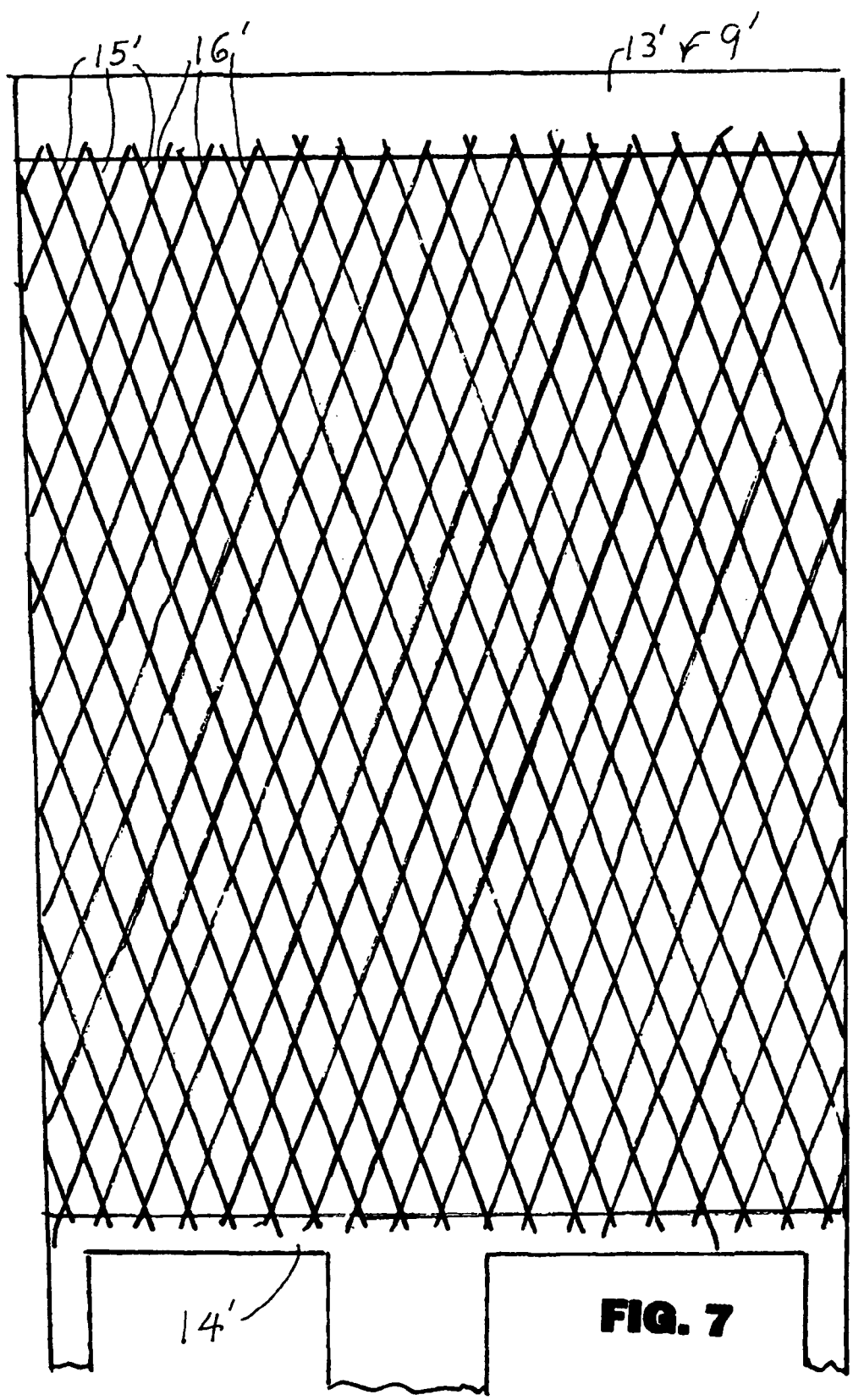
FIG. 7 is a plan view of the mesh fabric member of another embodiment of the invention.
Figure 8:
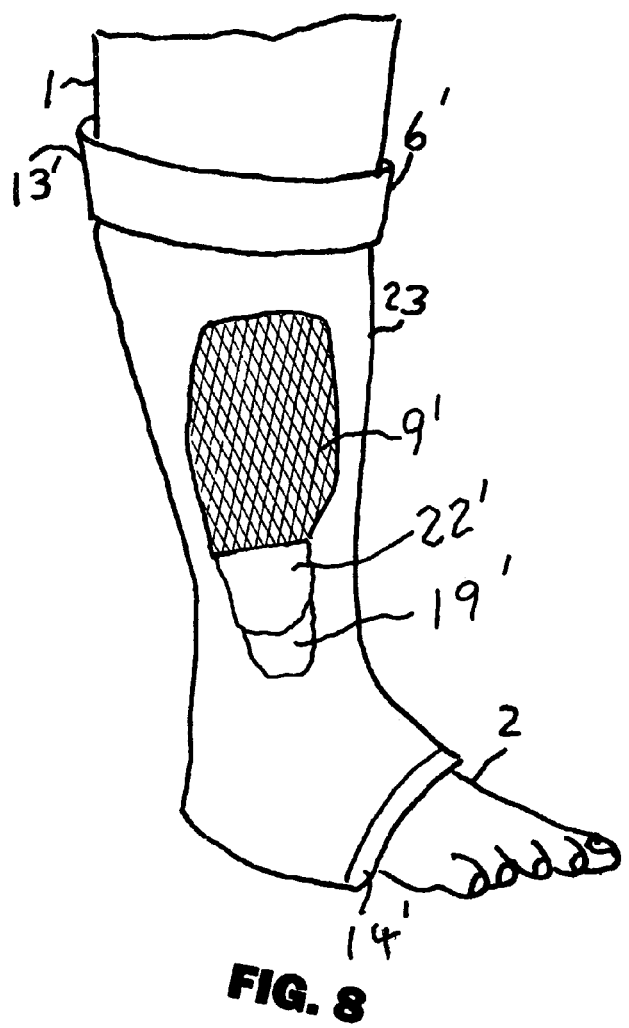
FIG. 8 is a perspective view of a liner of the invention, partially cut away, in a leg cast.

Referring now to FIGS. 7 and 8, a leg cast 23 is shown with a portion cut away to reveal the liner 6' with inner layer 19', mesh member 9' and outer layer 22'. The mesh comprises a plurality of first parallel fibersl 5' disposed transverse to a plurality of second parallel fibers 16'. Both ends of fibers 15' and 16' are attached to the proximal terminal element 13' and the distal terminal element 14' that are releasably attached to the outside ends of the cast. When the cast becomes loose, such as by reduction of swelling, either element 13' or 14' may be released, pulled away from the end of the cast until the desired tightening is achieved, and the element reattached to the end of the cast.

Figure 9:
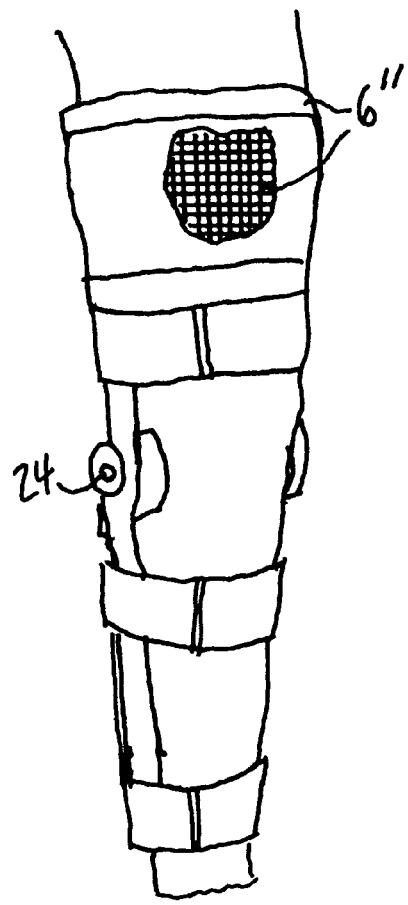
FIG. 9 is a perspective view of a liner of the invention, partially cut away, in a knee brace.

Referring now to FIG. 9, a knee brace is shown partially cut away to show a liner 6" of the invention. The brace is mounted so that the pivot element 24 of the brace will be aligned with the knee pivot. If the brace slips down on the leg until the brace pivot is not aligned with the knee pivot, normal knee motion will be impaired. The liner of the invention enables the user to tighten the brace around the knee by simply releasing one end of the liner from an outer surface of the brace, without removing the brace, and pulling it until the desired tightness is achieved. The end is then reattached to the end of the brace.

When the liner is used with a brace that encloses a joint, the mesh fabric member may have the active longitudinal fibers that tighten limited to the sides of the joint by the following method. A mesh fabric with all of the longitudinal fibers connected to both ends is wrapped around the leg. The anterior and posterior fibers are then cut from both ends. The lateral longitudinal fibers are then alternately cut from one or the other of the ends, so that limb bending does not actuate compression.

It will be understood that certain changes in form and arrangement of parts and the specific manner of practicing the invention may be made within the underlying idea or principles of the invention.

What is claimed is:

1. Apparatus comprising:

a rigid cast for encircling a limb;

a multilayer sleeve liner for the cast adapted to encircle the limb under the cast, the liner comprising:

a soft resilient first layer having cushioning and moisture absorbing properties for applying to skin beneath the cast;

a compressive second layer for encircling the first layer after the first layer has been fitted and applied to the skin, the compressive layer comprising:

f) a plurality of parallel first fibers;

g) a plurality of parallel second fibers disposed transverse to the first fibers to form a mesh fabric, the mesh fabric having a first termination and a second termination;

h) hook and loop attaching means affixed to an exterior surface of a first end of the cast and to the first termination for releasably attaching the first termination to the first end of the cast;

i) attaching means for attaching the second termination to a second end of the cast;

j) the compressive layer constructed to adjustably apply compression to the skin when longitudinal stress is adjustably applied to the layer by releasing the first termination from the first end of the cast, either moving the first termination away from the second termination to increase compression, or moving the first termination toward the second termination to reduce compression, and then attaching the first termination to the first end of the cast; and adjacent second fibers having two ends, the second fibers being not attached to a termination at one end, and being affixed alternately to the first termination and the second termination at the other end.

2. The apparatus of claim 1 further comprising a third layer, the third layer disposed between the second layer and the cast, the third layer constructed to prevent the cast from adhering to the second layer.

3. A multilayer sleeve liner for a cast encircling the skin of a limb, the liner comprising:

a compressive member for encircling a portion of the limb within the cast, the compressive member comprising;

a) a plurality of parallel first fibers;

b) a plurality of parallel second fibers disposed transverse to the first fibers to form a mesh fabric, the mesh fabric having a first termination and a second termination;

c) attaching means for releasably attaching the first termination to a first end of the cast;

d) attaching means for attaching the second termination to a second end of the cast;

e) the first fibers disposed at right angles to the second fibers and a long axis of the cast;

f) adjacent second fibers unattached to a termination at one end, and with the other end affixed alternately to the first termination and the second termination;

g) intersections of the first fibers with the second fibers include an attachment of the first fiber to the second fiber; and h) the compressive member constructed to adjustably apply compression to the skin when longitudinal stress is adjustably applied to the member by releasing the first termination from the first end of the cast, either moving the first termination away from the second termination to increase compression, or moving the first termination toward the second termination to reduce compression, and then attaching the first termination to the first end of the cast.

4. The sleeve liner of claim 3 further comprising a soft resilient first layer having cushioning and moisture absorbing properties for applying to the skin before applying the compressive member.

5. The sleeve liner of claim 4 further comprising a third layer disposed between the compressive member and the cast, the third layer constructed to prevent the cast from adhering to the compressive member.

6. The sleeve liner of claim 3 further Comprising an encircling layer disposed between the compressive member and the cast, the encircling layer constructed to prevent the cast-from adhering to the compressive member.

* * * * *